United States Patent
Benson et al.

(10) Patent No.: US 10,238,591 B2
(45) Date of Patent: Mar. 26, 2019

(54) COSMETIC COMPOSITIONS COMPRISING ESTOLIDE ESTERS AND USES FOR HAIR TREATMENT

(71) Applicant: Clariant International Ltd., Muttenz (CH)

(72) Inventors: Hannah Benson, Bensheim (DE); Katarzyna Kita-Tokarczyk, Bad Soden (DE); Dirk Leinweber, Kelkheim (DE); Henrike Neuhoff, Hannover (DE); Anton Kratz, Frankfurt am Main (DE); Steffen Romanski, Frankfurt (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/569,696

(22) PCT Filed: Apr. 29, 2016

(86) PCT No.: PCT/EP2016/059707
§ 371 (c)(1),
(2) Date: Oct. 26, 2017

(87) PCT Pub. No.: WO2016/174256
PCT Pub. Date: Nov. 3, 2016

(65) Prior Publication Data
US 2018/0125767 A1    May 10, 2018

(30) Foreign Application Priority Data

Apr. 30, 2015 (EP) .................................... 15001296
Oct. 30, 2015 (EP) .................................... 15192472

(51) Int. Cl.
*A61K 8/37* (2006.01)
*A61Q 5/02* (2006.01)

(52) U.S. Cl.
CPC ................. *A61K 8/37* (2013.01); *A61Q 5/02* (2013.01); *A61K 2800/48* (2013.01); *A61K 2800/596* (2013.01)

(58) Field of Classification Search
CPC .......... A61K 2800/48; A61K 2800/596; A61K 8/37; A61Q 5/02
See application file for complete search history.

(56) References Cited

U.S. PATENT DOCUMENTS

| 6,051,214 A | 4/2000 | Isbell | |
|---|---|---|---|
| 2011/0282084 A1* | 11/2011 | Potula | C07C 67/08 554/156 |
| 2013/0065970 A1* | 3/2013 | Bredsguard | A61K 8/37 514/785 |
| 2013/0340649 A1 | 12/2013 | Ogura | |
| 2014/0315996 A1 | 10/2014 | Pilz | |
| 2014/0323592 A1 | 10/2014 | Pilz | |
| 2014/0329870 A1 | 11/2014 | Pilz | |
| 2014/0343171 A1 | 11/2014 | Pilz | |
| 2014/0348763 A1 | 11/2014 | Pilz | |
| 2014/0369943 A1 | 12/2014 | Pilz | |

FOREIGN PATENT DOCUMENTS

| EP | 2739136 A1 | 6/2014 |
|---|---|---|
| EP | 2739146 A1 | 6/2014 |
| EP | 2739147 A1 | 6/2014 |
| EP | 2739148 A1 | 6/2014 |
| EP | 2739149 A1 | 6/2014 |
| EP | 2739151 A1 | 6/2014 |
| EP | 2739152 A1 | 6/2014 |
| JP | H05331027 | 12/1993 |
| JP | H05331028 | 12/1993 |
| WO | WO 0018363 A1 | 4/2000 |

(Continued)

OTHER PUBLICATIONS

International Search Report for PCT/EP2016/059707, dated Jul. 8, 2016.
Jumat Salimon et al: "Synthesis and Physical Properties of Estolide Ester Using Saturated Fatty Acid and Ricinoleic Acid", Journal of Automated Methods and Management in Chemistry, vol. 73, No. 5, Dec. 31, 2011 (Dec. 31, 2011), pp. 563-564.
Database GNPD [online] MINTEL; Dec. 31, 2012 (Dec. 31, 2012), "Hair loss adjuvant treatment advance shampoo", XP002742536, Database accession No. 1938833.

(Continued)

*Primary Examiner* — Ernest V Arnold
(74) *Attorney, Agent, or Firm* — Tod A. Waldrop

(57) ABSTRACT

Cosmetic compositions comprising water, at least one estolide ester compound of Formula (3) wherein n is from 1 to 10, preferably from 2 to 8, and R is selected from branched or linear $C_{3-20}$-alkyl, and B) optionally at least one surfactant component B, C) optionally at least one thickener component C, D) optionally at least one hair conditioning component D, and E) optionally at least one further component E, different to A to D, can be used for improved hair treatment.

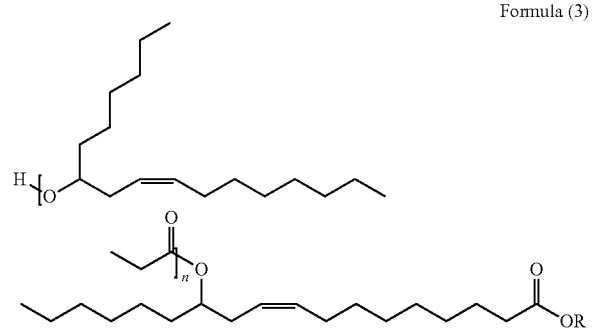

Formula (3)

20 Claims, No Drawings

(56) References Cited

FOREIGN PATENT DOCUMENTS

| WO | WO 2013009471 A1 | 1/2013 |
|----|------------------|--------|
| WO | WO 2013-017256   | 6/2014 |
| WO | WO 2013-017257   | 6/2014 |
| WO | WO 2013-017258   | 6/2014 |
| WO | WO 2013-017262   | 6/2014 |
| WO | WO 2013-017263   | 6/2014 |
| WO | WO 2013-017264   | 6/2014 |

OTHER PUBLICATIONS

English Abstract of WO 2013-017263, Feb. 7, 2013.
English Abstract of JPH05331027, Dec. 14, 1993.
English Abstract of JPH05331028, Dec. 14, 1993.

* cited by examiner

COSMETIC COMPOSITIONS COMPRISING ESTOLIDE ESTERS AND USES FOR HAIR TREATMENT

The present invention relates to a cosmetic composition, in particular to a hair care composition comprising at least one estolide ester compound derived from ricinoleic acid, and to methods of preparing the same. The cosmetic compositions according to the invention are in particular for use as hair shampoo and/or conditioning compositions.

Human hair contains approximately 97% of the protein keratin, which needs to be protected against environmental influences to preserve hair's strength and natural look. Therefore, suitable cleaning and conditioning compositions for hair are needed.

The use of simple curd soap would lead to a degeneration of the natural protective layer of the hair. Furthermore, typical hair treatments such as straightening, dyeing, permanent wave, or using hair spray can lead to damaged hair. Some results may be split ends, toneless, dry and/or dull hair. For these reasons, improved hair care compositions are required.

Many publications have been made about cosmetic hair care compositions. U.S. Pat. No. 6,051,214 and WO2000/18363 describe shampoo and conditioning compositions containing one or more fatty acid estolides of the general Formula (1).

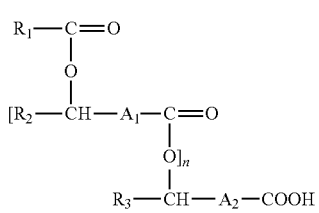

Formula (1)

WO2000/18363 is hereinafter referred to as Isbell et al. It is shown in Isbell et al. that these organic acid compounds, derived from oleic acid or from meadowfoam oil, can possess hair care properties and can be used, for example, in a shampoo. Isbell et al. relates exclusively to acids (see COOH group in Formula [1] above). Unfortunately, acids have the disadvantage of being prone to instability issues such as self-condensation over time. Furthermore, carboxylic acids are able to complex calcium in hard water causing them to precipitate out of solution. Furthermore, due to the COO$^-$ group, carboxylic acids repel other negatively charged material such as keratin fibres.

In WO 2013/009471, estolide ester compounds with potential use in personal care and cosmetic compositions are disclosed. Formula (2) of WO 2013/009471 encompasses a broad class of oligomer compounds.

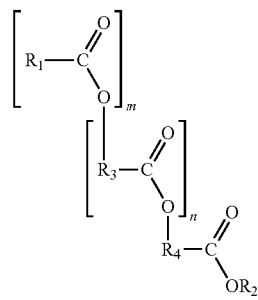

Formula (2)

The various residues $R_1$ to $R_4$ in this formula may be selected from several extended lists. Some examples of these estolide ester compounds are obtained by acid catalyzed addition of oleic acid.

There still is a great need for improved cosmetic compositions, in particular for hair treatment, and for new hair care compositions which, based on easily available components, protect against UV light, pollution and other negative influences of the environment. Particularly in cities with higher air pollution, the hair needs to be protected over a longer period of time. The hair should remain easy to comb and should keep a good level of gloss, even for long hair, over a longer period of time.

Furthermore there is a need for providing components for cosmetic compositions that are based on natural and renewable materials or derived therefrom. Indeed, consumers are, in present times, highly conscious as to the source of the components used in such composition and these consumers feel much more comfortable using components that are derived from natural and renewable materials. One objective of the present invention is therefore to provide a stable cosmetic composition for hair care products comprising components based on preferably renewable starting materials, more preferably natural renewable starting materials.

A further objective for the present invention is to provide more stable components for cosmetic compositions so that the compositions have a longer shelf life, as well as providing components that provide excellent performance in hard water areas.

General hair treatment compositions for hair care are known, however there is still a need of compositions designed for hair care, which are based on easily available components. These compositions can improve combing and gloss properties for several hair types. It now was found that specific types of estolide ester compounds are excellent components for cosmetic compositions, in particular for hair treatment.

Estolides are long-chain esters of the same or different (hydroxy) fatty acids or unsaturated fatty acids, made by acid-catalyzed addition. Estolide esters may be formed by esterification of an estolide with an alcohol, or directly by adding alcohols during the synthesis of estolides.

The present invention relates to cosmetic compositions comprising water and at least the following components:
A) at least one estolide ester compound having the Formula (3) as component A:

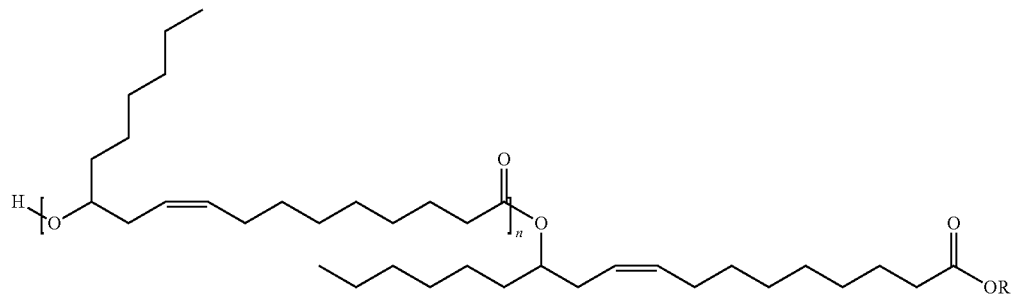

Formula (3)

wherein
n is from 1 to 10, preferably from 2 to 8, in particular from 3 to 7, and
R is selected from branched or linear $C_{3-20}$-alkyl, preferably from $C_{6-18}$-alkyl, more preferably $C_{10-16}$-alkyl, even more preferably $C_{12-14}$-alkyl,
B) optionally at least one surfactant component B,
C) optionally at least one thickener component C,
D) optionally at least one hair conditioning component D, and
E) optionally at least one further component E, different to components A to D.

According to the invention, the cosmetic composition contains component A, water and at least one component B or at least one component D. Preferably, the composition comprises the components A, B, C and E or the components A, C, D and E. These components are described in some more detail.

Component A

Component A (estolide ester) may be present in the composition in an amount of from 0.1 to 10% by weight, preferably of from 0.1 to 8% by weight, even more preferably of from 0.2 to 5% by weight, in particular of from 0.2 to 3% by weight, based on the total weight of the composition.

As used herein, the term "estolide ester" means an oligomeric fatty acid ester, wherein the monomers are joined by ester linkages. The term "estolide ester" is a term known in the art—see e.g. WO2013/009471.

In Formula (3), R is selected from branched or linear $C_{3-20}$-alkyl. In at least one embodiment, the composition comprises a mixture of Component A compounds having R being branched or linear $C_{3-20}$-alkyl. In other words, a mixture of compounds having alkyl chains within this carbon chain length range.

In at least one embodiment, R is selected from branched or linear $C_{6-12}$-alkyl, or from branched or linear $C_{6-11}$-alkyl, or from branched or linear $C_{6-10}$-alkyl. In at least one preferred embodiment, R is selected from branched or linear $C_{6-18}$-alkyl, more preferably branched or linear $C_{8-16}$alkyl, even more preferably branched or linear $C_{10-16}$-alkyl, most preferably branched or linear $C_{12-14}$alkyl. In at least one embodiment, the composition comprises a mixture of Component A compounds having R being branched or linear $C_{10-16}$-alkyl, for example the composition may comprise Component A compounds having R being linear or branched $C_{10}$-alkyl, and Component A compounds having R being linear or branched $C_{12}$-alkyl, and Component A compounds having R being linear or branched $C_{14}$-alkyl, and Component A compounds having R being linear or branched $C_{16}$-alkyl. In a particularly preferred embodiment, the composition comprises a mixture of Component A compounds having R being branched or linear $C_{12-14}$-alkyl.

Component A is at least one estolide ester compound having the Formula (3), wherein n is from 1 to 20, preferably from 1 to 15, even more preferably from 1 to 10, even more preferably from 2 to 8, and in particular from 3 to 7; and R is selected from branched or linear $C_{8-16}$alkyl.

In a preferred embodiment, the value of n in the compounds having the Formula (3) may be selected from 1 to 10, preferably from 1 to 9, even more preferably from 2 to 9 and in particular from 2 to 8, most preferably from 3 to 7. Preferably, component A is (or comprises) a trimer (n=2), a tetramer (n=3), a pentamer (n=4), a hexamer (n=5), a heptamer (n=6), an octamer (n=7), a nonamer (n=8), or mixtures thereof. In particular, component A is a tetramer (n=3), a pentamer (n=4), a hexamer (n=5), a heptamer (n=6), or mixtures thereof.

In a preferred embodiment, the residue R in the compounds of Formula (3) is selected from the group consisting of propyl, butyl, pentyl, hexyl, heptyl, octyl, nonyl, decanyl, undecanyl, dodecanyl, isopropyl, isohexyl, 2-methylhexyl, 2-ethylhexyl, 2-ethylheptyl, and 2-methyloctyl. R is in particular 2-ethylhexyl or decanyl.

Since R cannot be hydrogen, then Component A is not a carboxylic acid. Acids are not desired since they have the disadvantage of being prone to instability issues such as self-condensation over time. The present Component A in contrast provides excellent stability over time e.g. in storage. Furthermore, carboxylic acids are able to complex calcium in hard water causing them to precipitate out of solution. The present Component A is an ester and provides excellent performance in hard water areas. Furthermore, due to the $COO^-$ group, carboxylic acids repel other negatively charged material such as keratin fibres. The present Component A is an ester and is not negatively charged. Consequently, the present selection of R results in a Component A that provides excellent performance in a cosmetic composition suitable for application onto hair since Component A is not repelled by the negative charges on keratin fibres.

Formula (3) requires Component A to be unsaturated. Unsaturated compounds have the advantage that they typically have a lower melting points, higher solubility and higher biodegradability.

In at least one embodiment, Component A comprises one or several compounds of Formula (3) having the same n. Component A may be e.g. a compound of Formula (3), wherein n is 3.

In another preferred embodiment, Component A is a mixture of compounds of Formula (3), wherein n varies from 1 to 10. The number average molecular weight ($M_n$) of these mixtures may be determined by GPC (gel permeation chromatography). GPC can help to measure the molecular mass distribution of the estolide esters present in a mixture of compounds of Formula (3), e.g. when n is from 1 to 10.

Component A may be prepared by esterification starting from ricinoleic acid or from commercially available self-condensation products, such as Hostagliss® L2, L4, and L6 (of Clariant, DE). The number of Hostagliss® describes the average degree of oligomerization. L2 is a product mixture with an average molecular weight of dimers; L4 is a product mixture with an average molecular weight of tetramers and L6 is a product mixture with an average molecular weight of hexamers.

Preferably, 2 to 6 equivalents of ricinoleic acid are esterified with 0.5 to 2 equivalents of one or several branched or linear $C_{3-20}$-alkyl alcohols. The esterification may be acid-catalyzed. Suitable acid catalysts are e.g. hypophosphoric acid, methane sulfonic acid, p-toluene sulfonic acid, phosphoric acid, or sulfuric acid.

The component A can preferably possess a particular acid resistance. At room temperature (20° C.) and at 50° C., under acidic conditions (in sodium laureth sulfate solution, and in a formulated hair conditioner, pH 3), 99.99% by weight of the compound of Formula (3) remained stable over a period of one week. Ricinoleic acid was tested analytically as a decomposition product, and it was found that its level after one week at 50° C. was identical to the initial value, below 0.01% (detection limit of the method is 0.01%).

The composition contains at least one Component A. Preferably the composition contains more than one type of compound having the Formula (3).

Compounds of Formula (3) may be derived from R-ricinoleic acid, S-ricinoleic acid, or a mixture thereof. In a preferred embodiment, compounds having the Formula (3) contain more than 70% by weight of the R-ricinoleic acid stereoisomer. In another preferred embodiment, compounds having the Formula (3) contain more than 70% by weight of the S-ricinoleic acid stereoisomer.

In at least one embodiment, Component A of formula (3) has a hydroxyl value (OH value) from 1 to 60, preferred from 5 to 55, often from 5 to 46, in some cases from 10 to 46 mg KOH/g. The OH value herein is measured as per ASTM D5558-95 (2011). The OH value may also be analyzed using other known methods, such as ASTM D94-07 (2012), or DIN 51559-1 (2009-04). Hydroxyl value is a well-known parameter used in the art—see for example, EP2739147, EP2739149, EP2739146, EP2739152, EP2739148, EP2739136, EP2739151.

Increased hydroxyl values may also result from unreacted alcohol in the mixture, so this parameter does not fully characterize the reaction product, if this still contains unreacted alcohol. Acid number can also be used: a lower acid number indicates a lower amount of residual non-esterified estolide, and thus higher estolide ester content. Acid numbers for estolide esters described here are lower than 20 (in a preferred embodiment lower than 10). The acid value may be analyzed using methods such as DIN EN ISO 2114.

In at least one embodiment Component A has a number average molecular weight ($M_n$) from 600 to 6000 g/mol, preferably from 900 to 5000 g/mol, even more preferably from 1000 to 3500 g/mol, even more preferably from 1100 to 3000 g/mol, in particular from 1200 to 2200 g/mol. The molecular weight may be measured using high-performance liquid chromatography (HPLC), such as size exclusion chromatography (SEC), in particular gel permeation chromatography (GPC).

Ricinoleic acid is a natural occurring fatty acid and therefore a renewable material. In at least one embodiment, component A is derived from 100% natural and renewable materials. Further, the corresponding esters according to the invention normally lack nitrogen- or ammonium-moieties. Therefore, component A is ideal for the application for eco-friendly shampoos and conditioners, which are especially needed for hair treatment for outdoor activities, and for products with eco-friendly labels for environmentally conscious consumers.

Component B

The composition comprises optionally at least one surfactant component B. As used herein, "surfactant" means a surface-active agent. In at least one embodiment, the surfactant is an organic amphiphilic compound having at least one hydrophobic portion and at least one hydrophilic portion.

The (cleansing) surfactant, component B, may be selected from the group consisting of anionic, non-ionic, betaine, and amphoteric surfactants. Component B may be present in the composition in an amount of from 0 to 80% by weight, preferably of 1 to 50% by weight, more preferably from 5 to 20% by weight, based on the total weight of the composition.

In a preferred embodiment for a shampoo composition, surfactant component B may be present in the composition in an amount of from 0 to 80% by weight, preferably of from 1 to 50% by weight, even more preferably of from 2 to 25% by weight, in particular of from 5 to 25% by weight, based on the total weight of the composition.

In a preferred embodiment of a conditioning and a leave-on conditioning composition, surfactant component B may be present in the composition in an amount of from 0 to 20% by weight, preferably of from 0 to 10% by weight, even more preferably of from 0.01 to 5% by weight, in particular of from 0.1 to 1% by weight, based on the total weight of the composition.

In another preferred embodiment the surfactant component B is an anionic surfactant. Ammonium lauryl ether sulfate and sodium lauryl ether sulfate (SLES) are particularly preferred surfactants for use in hair care compositions of this invention. Specific examples of other suitable anionic surfactants include polyoxyethylene alkyl ether sulfates such as sodium laureth sulfate (EMAL® 227E, Kao Chemicals), isethionate, taurate, sodium $C_{14-16}$ olefin sulfonate, ammonium $C_{12-15}$ pareth sulfate, sodium myristyl ether sulfate, or polyoxyethylene alkyl sulfates such as triethanolamine lauryl sulfate, sodium lauryl sulfate, disodium monooleamidosulfosuccinate, ammonium lauryl sulfosuccinate, sodium dodecylbenzene sulfonate, triethanolamine dodecylbenzene sulfonate, and sodium N-lauroyl sarcosinate.

In another preferred embodiment the surfactant component B is a non-ionic surfactant, which may be selected from alkoxylated derivatives of the following: fatty alcohols, alkyl phenols, fatty acids, fatty acid esters and fatty acid amides, in the $C_{16}$ to $C_{40}$ range, and having from about 1 to about 110 alkoxy groups. The alkoxy groups are selected from the group consisting of $C_{2-6}$ oxides and their mixtures, with ethylene oxide, propylene oxide, and their mixtures being the typical alkoxides. The alkyl chain may be linear, branched, saturated, or unsaturated. Of these alkoxylated nonionic surfactants, the ethoxylated alcohols and propoxylated alcohols are preferred. The alkoxylated alcohols may be used alone or in mixtures.

Commercially available nonionic surfactants are exemplarily Brij® from Uniqema, Willmington (USA). Typically, Brij® is the condensation product of aliphatic alcohols with ethylene oxide. The alkyl chain of the alcohol typically is a linear chain and having from about 8 to about 22 carbon atoms. The ethylene oxide typically is used in a range of from about 1 to about 54 moles. Examples are Brij® 72 (i.e., Steareth-2) and Brij® 76 (i.e., Steareth-10).

Other nonionic surfactants suitable for use in the present invention are alkyl glycosides, which are the condensation products of long chain alcohols, e.g. $C_{8-30}$ alcohols, with sugar or starch polymers. Commercially available examples of these surfactants include decyl polyglucoside (available as APG® 325 CS) and lauryl polyglucoside (available as APG® 600CS and 625 CS), available from Cognis, Ambler. Also suitable are glucamide surfactants (Clariant, Germany), for example those under the brand name of Gluco-Tain® or GlucoPure. Also useful herein as nonionic surfactants are sorbitan esters such as sorbitan monopalmitate, Polysorbat 20 or Polysorbat 80. Sorbitan esters may comprise mixtures of mono-, di-, tri-, etc. esters. Representative examples of suitable sorbitan esters include sorbitan monooleate, sorbitan stearates, sorbitan monoisostearate, and sorbitan sesquioleate.

In another preferred embodiment nonionic surfactants are glyceryl esters and polyglyceryl esters, including glyceryl monesters, typically glyceryl monesters of $C_{16-22}$ saturated, unsaturated, linear and branched chain fatty acids such as glyceryl oleate, glyceryl monostearate, glyceryl monoisostearate, glyceryl monopalmitate, glyceryl monobehenate, and mixtures thereof.

Also useful herein as nonionic surfactant may be selected from the group comprising fatty acid diethanolamides (DEA). Typical examples are isostearic acid DEA, lauric acid DEA, capric acid DEA, linoleic acid DEA, myristic acid DEA, oleic acid DEA, and stearic acid DEA.

Further nonionic surfactants are selected from the group comprising fatty acid monoethanolamides such as coconut fatty acid monoethanolamide, fatty acid monisopropanolamides such as oleic acid monoisopropanolamide, lauric acid monoisopropanolamide, alkyl amine oxides such as N-cocodimethylamine oxide, N-lauryl dimethylamine oxide, N-myristyl dimethylamine oxide, and N-stearyl dimethylamine oxide, N-acyl amine oxides such as N-cocoamidopropyl dimethylamine oxide and N-tallowamidopropyl dimethylamine oxide, and N-alkoxyalkyl amine oxides such as bis(2-hydroxyethyl)$C_{12-15}$ alkoxy-propylamine oxide.

In another preferred embodiment the surfactant component B is an amphoteric surfactant, which can act as anionic surfactant in an alkaline solution or as cationic surfactant in an acidic solution. Examples are cocoamphocarboxyglycinate, cocoamphocarboxypropionate, cocobetaine, cocamidopropyl betaine, N-cocamidopropyldimethylglycine, N-lauryl-N-carboxymethyl-N-(2-hydroxyethyl)ethylenediamine.

Betaines such as alpha-(tetradecyldimethylammonio) acetate, beta-(hexadecyldiethylammonio) propionate, and gamma-(dodecyldimethylammonio) butyrate and sultaines such as 3-(dodecyldimethylammonio)-propane-1-sulfonate, and 3-(tetradecyldimethylammonio)ethane-1-sulfonate are named.

The above-mentioned surfactants can be used alone or in combination in the compositions according to this invention.

This component B should be different from components A, C, D and E.

Component C

The composition comprises optionally at least one thickener component C. As used herein, the term "thickener" means a thickening agent. In at least one embodiment, the thickener is a compound capable of increasing the viscosity of the composition versus the composition without such compound. In at least one embodiment, the thickener is a rheology modifying agent.

The cosmetic composition of the invention can contain from 0 to 10% by weight, preferably from 0 to 5% by weight, even more preferably from 0.01 to 5% by weight, in particular from 0.05 to 2% by weight, based on the total weight of the composition, of at least one rheology modifying agent, in particular thickener component C.

Suitable examples herein are cellulosic thickeners, hydroxyethyl-cellulose, hydroxypropylcellulose, and carboxymethylcellulose, guar gum, such as hydroxypropylguar, gums of microbial origin, such as xanthan gum and scleroglucan gum, and synthetic thickeners, such as crosslinked homo- or copolymers of acrylic acid such as carbomer and/or of acrylamidopropanesulphonic acid.

This component C should be different from components A, B, D and E.

Component D

The composition comprises optionally at least one hair conditioning component D. As used herein, the term "hair conditioning component" means a compound capable of conditioning keratin fibres, such as human hair. The cosmetic composition of the invention can contain from 0 to 25% by weight, preferably from 0 to 15% by weight, even more preferably from 0.1 to 10% by weight, in particular from 0.1 to 5% by weight, based on the total weight of the composition, of a hair conditioning component D. This component D should be different from components A, B, C and E.

Conditioning component D may be any known in the art conditioning agent, but preferably selected from the group consisting of cationic surfactants, silicones, quaternary ammonium compounds, and natural or synthetic cationic polymers.

Cationic components, which are not washed out completely may be suitable for compositions according to the invention. The hydrophilic ends of the cationic components can bind to the keratin, which contains negatively charged amino acids, whereas the hydrophobic ends of the molecules protect the hair surface.

Preferably, the cationic surfactants are cationic quaternary ammonium compounds, amide or amine conditioning agents, and cationic polymers. Suitable classical cationic conditioning agents include cationic quaternary ammonium salts. Examples of such salts include those having the Formula (4):

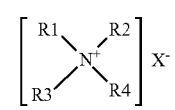

Formula (4)

wherein

N⁺ is a positively charged nitrogen atom,

R1 is an aliphatic group of $C_{1-22}$ alkyl, or aryl (such as phenyl), or alkyl-aryl group having 12 to 22 carbon atoms;

R2 and R3 are each independently an aliphatic group having $C_{1-22}$ alkyl; and R4 is a $C_{1-3}$ alkyl group, and X⁻ is an anion selected from halogen (such as Cl⁻), acetate, phosphate, nitrate and methyl sulfate radicals.

The aliphatic groups may contain, in addition to carbon atoms, ether linkages as well as amide groups. Suitable quaternary ammonium compounds may be mono-long chain alkyl, di-long chain alkyl, tri-long chain alkyl, and the like.

Examples of such quaternary ammonium salts of Formula (4) include benzalkonium chloride, benzyl triethyl ammonium chloride, cetyltrimethylammonium chloride (CTAC), behentrimmonium chloride (BTAC) and cetylpyridinium chloride.

Also suitable are amidoamine salts, which are the condensation products of fatty acids with polyfunctional amines. Exemplarily those having the formula R'CONH$(CH_2)_n NR^1R^2$, wherein R'CO is a fatty acyl group such as stearoyl, $R^1$ and $R^2$ are methyl or ethyl, and n is 2 or 3. Examples of such compounds include stearamidopropyl dimethylamine, see Alzo, Inc. product NECON®. Also suitable are salts of fatty primary, secondary, or tertiary amines, wherein the substituted groups have from 12 to 22 carbon atoms. Examples of such amines include dimethyl stearamine, dimethyl soyamine, stearylamine, myristylamine, tridecylamine and -ethyl stearamine.

As cationic components, a variety of synthetic cationic polymers are suitable, including quaternized cellulose ethers, copolymers of vinylpyrrolidone, acrylic polymers, including homopolymers or copolymers of dimethyldiallylammonium chloride and acrylamide. Such compounds are sold under MERQUAT® (Merck). Also suitable are various types of homo- or copolymers derived from acrylic or methacrylic acid, acrylamide, methylacrylamide, diacetone acrylamide.

Silicones are typical glossers such as dimethicone or cyclomethicone. Suitable as silicones are volatile or non-volatile nonionic silicone fluids, silicone emulsions, silicone resins, and silicone semisolids or solids. Volatile silicones are linear or cyclic silicones having a measureable vapor pressure, which is defined as a vapor pressure of at least 2 mm of mercury at 20° C. Also suitable are water insoluble nonvolatile silicone fluids including polyalkyl siloxanes such as polydimethyl siloxanes; polyaryl siloxanes; polyalkylaryl siloxanes such as polymethylphenylsiloxanes; polyether siloxane copolymers such as polypropylene oxide modified dimethylpolysiloxane; amine-functional silicones, and mixtures thereof.

Component E

The cosmetic composition of the invention can contain from 0 to 80% by weight, preferably from 0 to 50% by weight, even more preferably from 0.01 to 10% by weight, in particular from 0.1 to 8% by weight, based on the total weight of the composition, of a further component E. Component E is different to components A to D.

Component E exemplarily is a color altering component, a developer component, a pre-treatment component and/or a post-treatment component.

Such ingredients include well-known conventional additives, typically employed in hair treatment compositions, such as coloring agents, basifying and acidifying agents (such as citric acid or sodium hydroxide), buffers, gelling agents, rheological modifiers different to component C such as sodium chloride, emulsifiers, antioxidants, all fragrances known in the art such as linear and cyclic terpenes, and chelating agents.

Further, component E may be selected from the group consisting of acidity regulators (to maintain the hair care composition's pH at about 3 to 6), antistatic agents different to component B and D, lubricants such as fatty alcohols such as Cetearyl alcohol or pro-vitamins such as panthenol, moisturizers such as humectants, glycerin and ethylene glycol, oils such as natural oils and organic oils, preservatives such as benzoic acid, Quaternium-15, and DMDM hydantoin, sequestrants, strengtheners such as containing hydrolyzed protein, plant extracts, vitamins such as vitamin C, sun protectors such as benzophenone and titanium dioxide, and thermal protectors e.g. heat-absorbing components.

Components E can also be suitable oils, including esters of the formula R'CO—OR", wherein R' and R" are each independently a $C_{4-20}$ straight or branched chain alkyl, alkenyl or alkoxy-carbonylalkyl or alkylcarbonyl-oxyalkyl. Examples of such esters include isotridecyl isononanoate, PEG-4 diheptanoate (PEG=polyethyleneglycol), isostearyl neopentanoate, tridecyl neopentanoate, cetyl octanoate, cetyl palmitate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol.

The oil may comprise glyceryl esters of fatty acids, or triglycerides, such as castor oil, lanolin oil, triisocetyl citrate, $C_{10-18}$ triglycerides, caprylic/capric/triglycerides, coconut oil, mineral oil, almond oil, apricot kernel oil, avocado oil, babassu oil, evening primrose oil, camelina *sativa* seed oil, grape seed oil, macadamia *ternifolia* seed oil, corn oil, meadowfoam seed oil, mink oil, olive oil, palm kernel oil, safflower oil, sesame oil, soybean oil, sunflower oil, wheat germ oil and *camellia reticulata* seed oil.

Also suitable as the oils are glyceryl esters (excluding fats and oils which are glyceryl esters of fatty acids) which are primarily fatty acid mono-, di-, and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates and PEG glyceryl tallowates. Also suitable as the organic oil are non-volatile hydrocarbons such as isoparaffins, hydrogenated polyisobutene, mineral oil and squalene. Also suitable as the oil are various lanolin derivatives such as acetylated lanolin, acetylated lanolin alcohol, and various fluorinated oils, such as fluoro Guerbet esters or perfluoropolyethers. Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, and sorbitan tristearates.

The cosmetic composition may be prepared by mixing at least one component A with water and at least one component B and/or D. Optionally, at least one component C and/or at least one component E may be added to the composition.

Shampoo compositions according to the invention may comprise—based on the total weight of the composition:
from 0.5 to 20% by weight, preferably from 0.5 to 5% by weight of component A,
from 1 to 80% by weight, preferably from 5 to 20% by weight of component B,
from 0 to 30% by weight, preferably from 0.05 to 5% by weight of component C,
from 0 to 20% by weight, preferably from 0.1 to 5% by weight of component D,
from 0 to 30% by weight, preferably from 0.1 to 10% by weight of component E,
and water.

Conditioning compositions according to the invention may comprise—based on the total weight of the composition:
from 0.1 to 20% by weight, preferably from 0.2 to 5% by weight of component A,
from 0 to 30% by weight, preferably from 0 to 5% by weight of component B,
from 0 to 20% by weight, preferably from 0 to 5% by weight of component C,
from 0 to 30% by weight, preferably from 0.1 to 15% by weight of component D,
from 0 to 80% by weight, preferably from 0.1 to 8% by weight of component E,
and water. In a preferred embodiment a conditioning composition does not comprise component C.

In at least one embodiment, the conditioning compositions comprises from 67 to 99.6% by weight of water and
from 0.2 to 5% by weight of component A,
from 0 to 5% by weight of component B,
from 0.1 to 15% by weight of component D,
from 0.1 to 8% by weight of component E.

In at least one embodiment, the leave-on conditioning compositions comprises from 55 to 99.4% by weight of water and
from 0.01 to 5% by weight of component A,
from 0 to 5% by weight of component B,
from 0.01 to 5% by weight of component C,
from 0.5 to 20% by weight of component D,
from 0.01 to 10% by weight of component E.

In the method of the invention, the composition containing the cosmetic composition according to the invention is applied to the hair. Preferably, the composition containing the cosmetic composition is applied to wet hair. In at least one embodiment, the method according to the invention comprises applying the cosmetic composition according to the invention to the hair.

In a preferred embodiment first a shampoo composition comprising the cosmetic composition according to the invention is applied to the hair for a period of time ranging from about 10 seconds to 5 minutes. The shampoo composition is then rinsed from the hair using water. In a second step, the conditioning composition comprising the cosmetic composition according to the invention is applied to the hair. The conditioning composition may be left on the hair for about 1 to 10 minutes, or rinsed immediately, or as recommended in the instructions given in the kit. After the indicated amount of time has elapsed, the mixture is rinsed off the hair with water.

Optionally, a post-treatment composition, which may comprise compounds having the Formula (3), can be applied to the hair and may or may not be rinsed off. Following the application of the post-treatment composition, the hair may be styled as desired.

In another preferred embodiment a leave-on composition comprising the cosmetic composition according to the invention is applied to the dry or wet hair. After applying the leave-on conditioning composition according to the invention to wet hair, it may be dried by a dryer, a flat iron, a curling iron, a drying hood, or air. Subsequently the hair may be styled as desired. After applying the leave-on composition according to the invention to dry hair, it does not need any additional treatment but may be styled as desired.

The shampoo composition, and/or the conditioning composition, and/or the post-treatment composition, and/or the leave-on conditioning composition can be provided in a kit such that they may be used on a daily, bi-weekly or weekly basis, depending on the needs of the consumer. Preferably, the shampoo and conditioning compositions are used on a weekly to bi-weekly basis.

In another preferred embodiment, a composition comprising a combined composition of shampoo and conditioner, containing at least one compound having the Formula (3), is applied to the (wet) hair for a period of time ranging from about 10 seconds to 5 minutes.

The composition may be left on the hair for about 1 to 10 minutes, or rinsed immediately, or as recommended in the instructions given in the kit. After the indicated amount of time has elapsed, the mixture is rinsed off the hair with water.

The cosmetic composition comprising compounds having the Formula (3) are suitable for hair care of humans and animals. The invention is further illustrated by the following examples and the claims.

Methods Applied

The molecular weight is measured using gel permeation chromatography (GPC) using a modified styrene divinylbenzene copolymer as column material. The following columns are used: 1× guard column, 10 μm, 50 mm×8 mm ID and 2×GPC columns 100 Å, 5 μm, 300 mm×8 mm ID (PSS SDV).

Calibration is done with polystyrene in the range from 682 to 28000 g/mol, and detection is done with an evaporative light scattering detector (ELSD). Tetrahydrofurane is used as eluent, injection volume was 2 μL, and experiments are performed at 40° C. at the flow rate of 1.0 mL/min.

Hostagliss® L4 (Clariant, Frankfurt) is a self-condensation product mixture with an average molecular weight of tetramers (approximately 1300 g/mol). The viscosity (20° C.) is approximately 1100 mPa s (DIN ISO 53015, 2001-02).

For the calculation of the mass of Hostagliss® L4 and ricinoleic acid to be used in reactions to obtain compounds of the Examples 3, 5 and 6, the active levels of the acid (in technical grade materials) are calculated from the acid numbers which are determined experimentally.

EXAMPLE 1

Preparation of Estolide Ester from Hostagliss® L4 (of Clariant, Germany) and 2-Ethylhexanol.

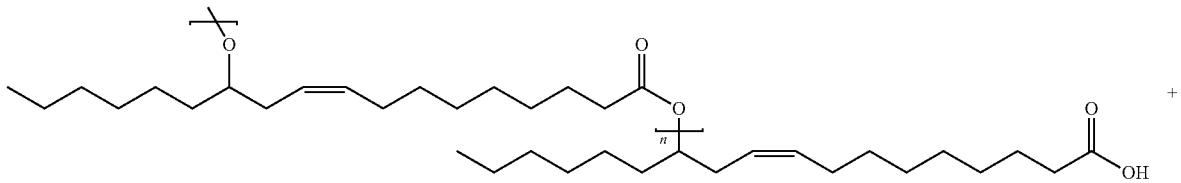

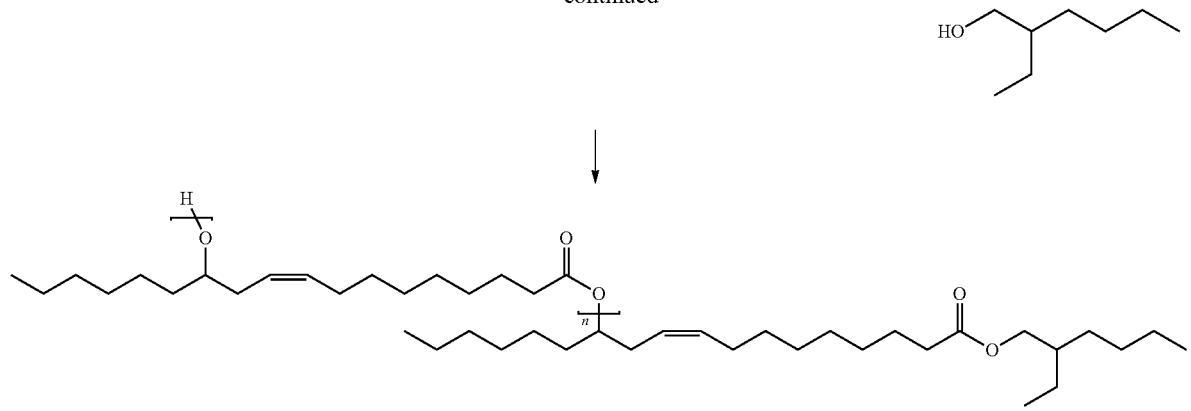

Hostagliss® L4 (300.1 g) is charged into a 1 L, 4-necked flask with a stirrer, a reflux condenser and a thermometer, and set under nitrogen atmosphere. Hypophosphoric acid (1.7 g) is added via a syringe and 2-ethylhexanol (34.3 g) is subsequently added drop-wise over a period of 10 min. The reaction mixture is heated to 160° C. and refluxed for one hour.

Subsequently the reflux condenser is replaced with a distillation bridge and the volatiles are distilled off over 19 h at 160° C. The product (276.9 g) is filled into a flask for storage and analyzed.

EXAMPLE 2

Preparation of Estolide Ester from Ricinoleic Acid (4 Eq.) and 2-Ethylhexanol

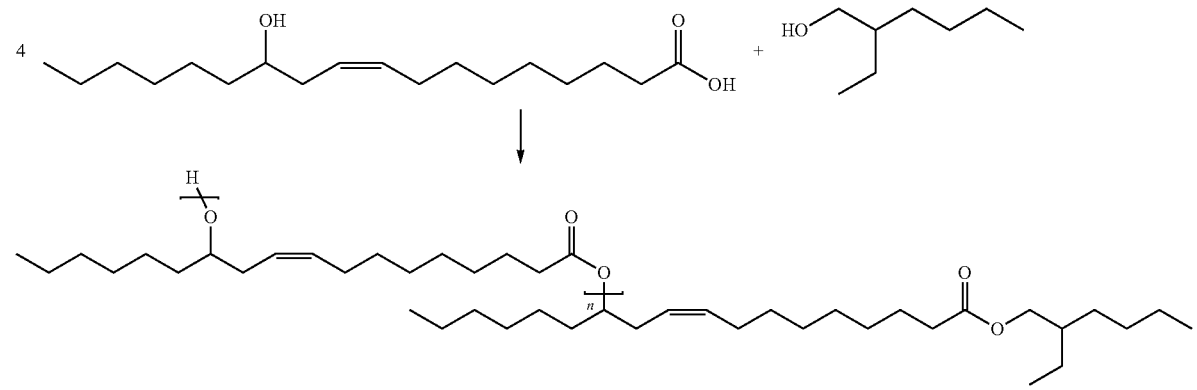

A 500 mL, 4-necked round bottom flask with stirrer, thermometer and a distillation bridge is set under nitrogen atmosphere and charged with ricinoleic acid (298.5 g) and 2-ethylhexanol (32.6 g). The reaction mixture is heated to 170° C. and the volatiles are distilled off for 4.5 h. Subsequently, methane sulfonic acid (0.56 g) is added and the reaction mixture is heated to 166-170° C. for 9 h and the volatiles are distilled off. The product (258.4 g) is filled into a flask for storage and analyzed.

EXAMPLE 3

Preparation of Estolide Ester from Ricinoleic Acid (2 Eq.) and 2-Ethylhexanol

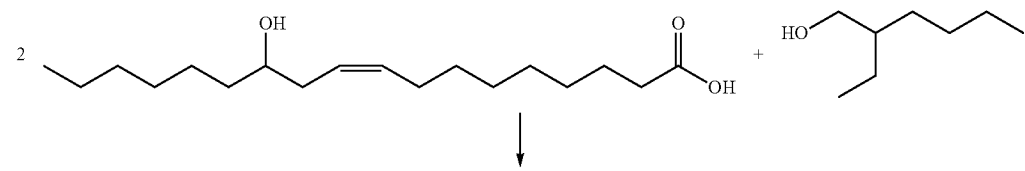

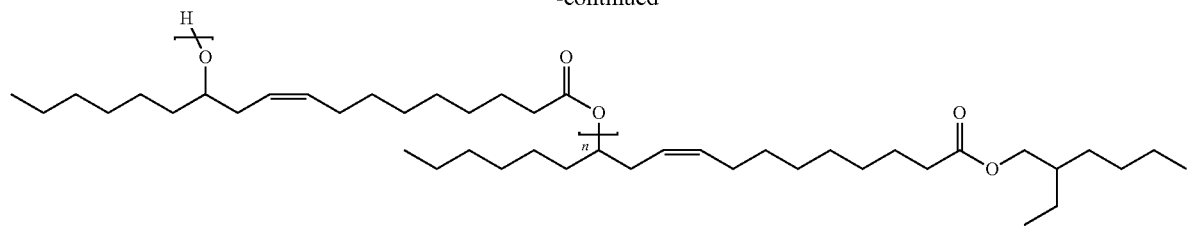

A 500 mL, 4-necked round bottom flask with stirrer, thermometer and a distillation bridge is set under nitrogen atmosphere and charged with ricinoleic acid (320.1 g) and 2-ethylhexanol (63.2 g). The reaction mixture is heated to 170° C. and the volatiles are distilled off for 3 h.

Subsequently, p-toluene sulfonic acid (0.95 g) is added and the reaction mixture is heated to 166-170° C. for 9 h and the volatiles are distilled off. The product (330.0 g) is filled into a flask for storage and analyzed.

EXAMPLE 4

Preparation of Estolide Ester from Hostagliss® L4 and Decanol

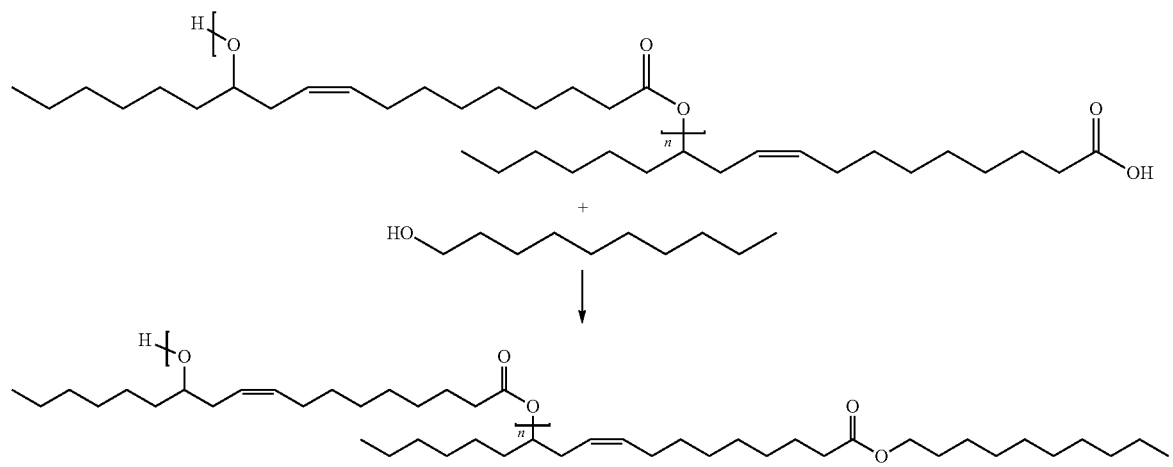

Hostagliss® L4 (300.0 g) is charged into a 500 mL, 4-necked flask with a stirrer, a reflux condenser and a thermometer and set under nitrogen atmosphere. Hypophosphoric acid (1.7 g) is added via a syringe and 1-decanol (41.6 g) is subsequently added drop-wise over a period of 10 min. The reaction mixture is heated to 155-165° C. and refluxed for one hour.

Subsequently, the reflux condenser is replaced with a distillation bridge and the volatiles are distilled off for 16 h at 165-178° C. The product (285.1 g) is filled into a flask for storage and analyzed.

EXAMPLE 5

Preparation of Estolide Ester from Ricinoleic Acid (2 Eq.) and Decanol

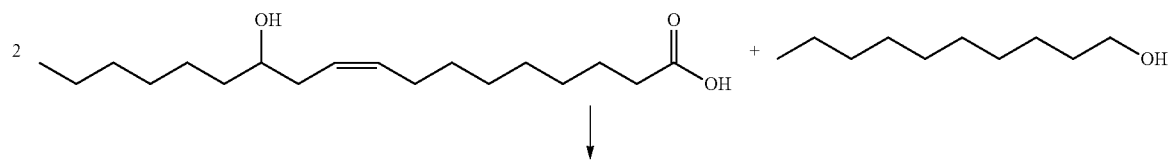

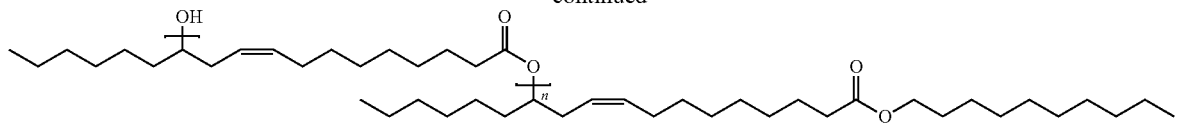

A 500 mL, 4-necked round bottom flask with stirrer, thermometer and a distillation bridge is set under nitrogen atmosphere and charged with ricinoleic acid (320.1 g) and 1-decanol (79.2 g). The reaction mixture is heated to 170° C. and the volatiles were distilled off for 5 h.

Subsequently, p-toluene sulfonic acid (0.95 g) is added and the reaction mixture is heated to 149-168° C. for 6 h and the volatiles are distilled off. The product (359.5 g) is filled into a flask for storage and analyzed.

EXAMPLE 6

Preparation of Estolide Ester from Ricinoleic Acid (4 Eq.) and Decanol

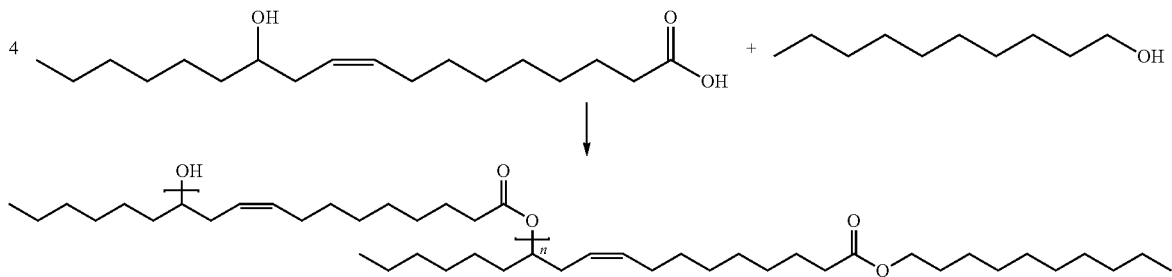

A 500 mL, 4-necked round bottom flask with stirrer, thermometer and a distillation bridge is set under nitrogen atmosphere and charged with ricinoleic acid (320.1 g) and 1-decanol (39.6 g). The reaction mixture is heated to 170° C. and the volatiles are distilled off for 4 h. Subsequently, p-toluene sulfonic acid (0.95 g) was added and the reaction mixture was heated to 156-174° C. for 33 h and the volatiles are distilled off.

The product (289.0 g) is filled into a flask for storage and analyzed.

EXAMPLE 6A

Preparation of estolide ester from ricinoleic acid (4 eq.) and Lauryl alcohol (dodecanol). Lauryl Alcohol can be purchased from Kao (Kalcol 2098).

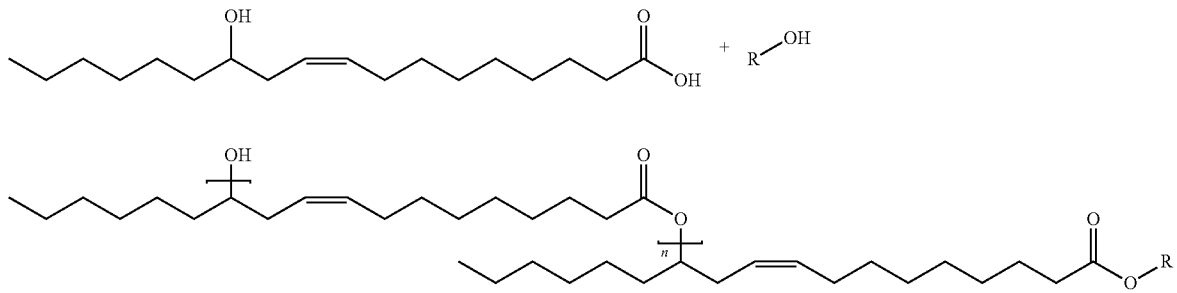

R = Lauryl Alcohol

A 500 mL, 4-necked round bottom flask with stirrer, thermometer and a distillation bridge is set under nitrogen atmosphere and charged with ricinoleic acid (320.1 g), p-toluene sulfonic acid (0.95 g) and 1-dodecanol (45.8 g). The reaction mixture is heated to 170° C. and the volatiles are distilled off for 13 h.

The product (312.3 g) is filled into a flask for storage and analyzed.

EXAMPLE 6B

Preparation of estolide ester from ricinoleic acid (4 eq.) and Lauryl-Myristyl alcohol. Lauryl-Myristyl alcohol can be purchased from Wilmar (Wilfarol 1214).

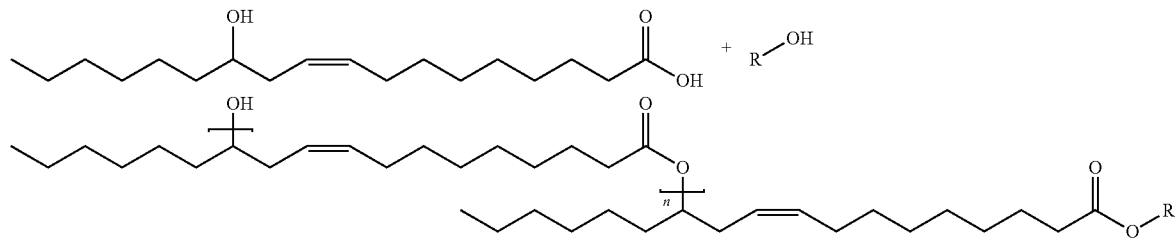

R = Lauryl-Myristyl Alcohol

A 500 mL, 4-necked round bottom flask with stirrer, thermometer and a distillation bridge is set under nitrogen atmosphere and charged with ricinoleic acid (320.1 g), p-toluene sulfonic acid (0.95 g) and Lauryl-Myristyl alcohol (48.5 g). The reaction mixture is heated to 170° C. and the volatiles are distilled off for 13 h.

The product (312.3 g) is filled into a flask for storage and analyzed.

TABLE 1

Summary and analytical data of Example 1 to Example 6.

| Example number | Starting material (estolide or fatty acid) | Starting material (alcohol) | OH value (mg KOH/g) | $M_n$ (g/mol) | Acid value (mg KOH/g) |
|---|---|---|---|---|---|
| 1 | Hostagliss ® L4 | 2-ethylhexanol | 17 | 2029 | 4.8 |
| 2 | Ricinoleic acid (4 eq.) | 2-ethylhexanol | 19 | 2143 | 4.4 |
| 3 | Ricinoleic acid (2 eq.) | 2-ethylhexanol | 46 | 1261 | 4.0 |
| 4 | Hostagliss ® L4 | Decanol | 16 | 1973 | 4.3 |
| 5 | Ricinoleic acid (2 eq.) (4 eq.) | Decanol | 44 | 1886 | 2.2 |
| 6a | Ricinoleic acid (4 eq.) | Dodecanol | 15 | 1928 | 3.7 |
| 6b | Ricinoleic acid (4 eq.) | Lauryl-Myristyl-Alcohol | 12 | 1927 | 1.4 |

Preparation of Shampoo Compositions

Shampoo compositions according to the invention are prepared by mixing the components, as listed in Table 2.

All products are creamy white liquids with appearance and with excellent physical properties similar to typical hair shampoo products available on the market. The pH value of the compositions is adjusted to 6.

TABLE 2

Hair shampoo composition; component active levels are given in % by weight (active levels of ingredients); q.s. = quantum satis (amount which is needed).

| Ingredient | Component | Example 7 | Example 8 |
|---|---|---|---|
| Estolide ester of Example 1 | A | 0.80 | — |
| Sodium laureth sulfate (Genapol ® LRO) | B | 12.00 | 12.00 |
| Cocamidopropyl betaine (Genagen ® CAB) | B | — | 0.80 |
| Cationic guar (Jaguar ® C162) | C | 0.20 | 0.20 |
| Carbomer (Carbopol ® 980) | C | 0.40 | 0.40 |
| Silicone (Xiameter ® PMX200) | D | 1.50 | 1.50 |
| NaOH | E | 1.50 | 1.50 |
| Preservative | E | q.s. | q.s. |
| Water | | Ad. 100.00 | Ad. 100.00 |

The composition according to Example 7 is stable over more than 6 weeks and showed better hair treatment performance as compared to a betaine-containing Example 8. Examples 7 and 8 illustrate that estolide esters can replace secondary surfactants in shampoo compositions, but because of their conditioning properties they can also be considered as replacement of typical conditioning components, such as e.g. quats, silicones or oils.

EXAMPLES 9, 10, 11

Hair shampoo compositions having the same component amounts as given in Table 2 (Example 7) containing isethionates instead of SLES (Example 9) having the same component amounts as given in Table 2 (Example 7), or glycinates instead of SLES (Example 10, having the same component amounts as given in Table 2, Example 7), or taurates instead of SLES (Example 11, having the same component amounts as given in Table 2, Example 7) give similar benefits.

EXAMPLE 12

A hair shampoo composition having the same component amounts as given in Table 2 (Example 7), but containing 2.3% by weight estolide ester instead of 0.8% by weight estolide ester and 1.5% by weight silicone give similar benefits for the treatment of hair.

EXAMPLE 13

A hair shampoo composition having the same component amounts as given in Table 2 (Example 7), but containing cocamidopropyl betaine instead of the cationic polymer give similar benefits.

Use of the Shampoo Compositions

The studies are conducted with hair swatches (using dark brown, straight European hair tresses, from Kerling, 15 cm long, ca. 2.6 g hair each). These hair swatches are pre-treated (base wash with a 14% by weight sodium lauryl ether sulfate (SLES) solution), and then treated with the shampoo composition from Example 7, according to the steps:

a) wetting the hair;
b) applying shampoo composition;
c) lathering and massaging the shampoo into the hair;
c) removing (rinsing) the shampoo composition from the hair.

Combing Force Measurements

Wet and dry combing force is measured using the Diastron (UK) MTT175 (for dry combing—after at least 12 hours of drying time), swatches are pre-combed three times before the measurement.

Table 3 presents the wet (average) and dry (maximum) combing force (gram-force [gmf]) for hair treated with shampoo from Example 7.

As comparison, an analogous shampoo is used containing cocamidopropyl betaine (CapB) according to comparative Example 8 at the equivalent active level, 0.8% by weight (see compositions in Table 2).

TABLE 3

Wet and dry combing force (gmf) results of hair treated with shampoo composition (Example 7), compared to the composition according to Example 8 (0.8% CapB).

| Composition | Wet combing force (average) | Dry combing force (maximum) |
|---|---|---|
| Example 8 (Cap B) | 29.6 | 268.5 |
| Example 7 | 16.0 | 108.3 |

Table 3 demonstrates the surprising improvement of combing forces of hair treated with shampoo from Example 7, comprising compounds having the Formula (3) compared to hair treated with shampoo, comprising no estolide ester.

Furthermore, the dry hair after the treatment with shampoo composition (Example 7) shows good tactile results and led to nice hair appearance, without the greasy effect on the hair.

Hair Shine Measurements

After the use of the shampoo composition on hair swatches, the hair probes were tested for hair shine (using a Samba Hair System, from Bossa Nova Tech). This measurement technique allows for quantitative evaluation of the light intensity reflected from hair swatches mounted on a drum in a half-circle arrangement. The technique selectively analyzes the following components:

First reflection (SHINE): from the surface of the fibers, creates a shine band on hair Second reflection (CHROMA): reflection of the transmitted light off the bottom surface of the fibers—creates a band carrying color information specific to the fiber DIFFUSED LIGHT results from the internal scattering, and corresponds to 'bulk hair' shine and color intensity.

Results of the shine measurements are summarized in Table 4; for hair swatches treated with the composition (according to the invention of Example 7) show stronger shine than those treated with the comparative composition (Example 8) containing CapB.

TABLE 4

Hair shine results for swatches treated with the estolide shampoo and comparative shampoo (compositions from Table 2).

| Composition | Shine (luminance)) |
|---|---|
| Example 8 | 17.3 |
| Example 7 | 18.7 |

Table 4 demonstrates approximately 10% improvement of hair shine of hair treated with shampoo from Example 7, comprising compounds having the Formula (3) compared to hair treated with shampoo, comprising no estolide.

Preparation of Hair Conditioning Compositions

The rinse-off hair conditioning compositions (Examples 14 to 55) are prepared by mixing the components, as listed in Table 5.

All conditioning compositions are creamy, white viscous liquids with appearance and with excellent physical properties similar to typical hair conditioner products available on the market. The pH value of the compositions is adjusted to 4.

TABLE 5

Rinse-off hair conditioning compositions, component active levels are given in % by weight; q.s. = quantum satis (amount which is needed).

| Ingredient | Example | | | | | |
|---|---|---|---|---|---|---|
| | 14 | 15 | 16 | 17 | 18 | 19 |
| Cetearyl alcohol (component E) | 4.0 | 4.0 | 4.0 | 4.0 | — | 3.2 |
| Example 1 | 2.0 | — | — | — | 2.0 | 2.0 |
| Example 4 | — | 2.0 | — | — | — | — |
| Example 2 | — | — | 2.0 | — | — | — |
| Example 3 | — | — | — | 2.0 | — | — |
| Plantasens ® natural | — | — | — | — | 8.0 | 1.0 |

TABLE 5-continued

Rinse-off hair conditioning compositions, component active levels are given in % by weight; q.s. = quantum satis (amount which is needed).

| Ingredient | Example | | | | | |
|---|---|---|---|---|---|---|
| emulsifier HP30 (Glyceryl Stearate, Cetearyl alcohol, Sodium Stearyl Lactylate | | | | | | |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

| | 20 | 21 | 22 | 23 | 24 | 25 |
|---|---|---|---|---|---|---|
| Cetearyl alcohol (component E) | 3.2 | 4.0 | 4.0 | 4.0 | 4.0 | 4.0 |
| CTAC (cetrimonium chloride) | — | 0.1 | 0.3 | 2.0 | 0.1 | 0.1 |
| Example 1 | 2.0 | 2.0 | 2.0 | 2.0 | 1.9 | — |
| Example 4 | — | — | — | — | — | 1.9 |
| Plantasens ® natural emulsifier HP30 (Glyceryl Stearate, Cetearyl alcohol, Sodium Stearyl Lactylate | 2.0 | — | — | — | — | — |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

| | 26 | 27 | 28 | 29 | 30 | 31 |
|---|---|---|---|---|---|---|
| Cetearyl alcohol | 4.0 | 4.0 | 4.0 | 4.0 | 4.0 | 4.0 |
| CTAC (component D) | 0.2 | 0.3 | 0.4 | 0.5 | 0.4 | 0.4 |
| Example 1 | 1.8 | 1.7 | 1.6. | 1.5 | — | — |
| Example 4 | — | — | — | — | 1.6 | — |
| Example 2 | — | — | — | — | — | 1.6 |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

| | 32 | 33 | 34 | 35 | 36 | 37 |
|---|---|---|---|---|---|---|
| Cetearyl alcohol | 4.0 | 4.0 | 4.0 | 4.0 | 4.0 | 4.0 |
| CTAC (cetrimonium chloride) | 0.4 | — | — | — | — | — |
| BTAC (behentrimonium chloride) | — | 0.1 | 0.2 | 0.3 | 0.4 | 0.5 |
| Example 1 | — | 1.9 | 1.8 | 1.7 | 1.6 | 1.5 |
| Example 3 | 1.6 | — | — | — | — | — |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

| | 38 | 39 | 40 | 41 | 42 | 43 |
|---|---|---|---|---|---|---|
| Cetearyl alcohol | 4.0 | 4.0 | 4.0 | 4.0 | 4.0 | 4.0 |
| BTAC (behentrimonium chloride) | 0.6 | 0.7 | 0.8 | 0.9 | 1.0 | 1.1 |
| Example 1 | 1.4 | 1.3 | 1.2 | 1.1 | 1.0 | 0.9 |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

| | 44 | 45 | 46 | 47 | 48 |
|---|---|---|---|---|---|
| Cetearyl alcohol | 4.0 | 4.0 | 4.0 | 4.0 | 4.0 |
| BTAC (behentrimonium chloride) | 1.2 | 1.3 | 1.4 | 1.5 | 1.7 |
| Example 1 | 0.8 | 0.7 | 0.6 | 0.5 | 0.3 |
| Preservative | q.s. | q.s. | q.s. | q.s. | q.s. |
| Water | Ad. 100 | Ad. 100 | Ad. 100 | Ad. 100 | Ad. 100 |

| | 49 | 50 | 51 | 52 | 53 | 54 |
|---|---|---|---|---|---|---|
| Cetearyl alcohol | 4.0 | 4.0 | 4.0 | 4.0 | 4.0 | 4.0 |
| CTAC (cetrimonium chloride) | 0.1 | 0.2 | 0.3 | 0.4 | 0.5 | 0.1 |
| BTAC (behentrimonium chloride) | 0.1 | 0.2 | 0.3 | 0.4 | 0.5 | 0.9 |
| Example 1 | 1.8 | 1.6 | 1.4 | 1.2 | 1.0 | 1.0 |
| Preservative | q.s. | q.s. | q.s. | q.s. | q.s. | q.s. |
| Water | Ad. 100 | Ad. 100 | Ad. 100 | Ad. 100 | Ad. 100 | Ad. 100 |

TABLE 5-continued

Rinse-off hair conditioning compositions, component active levels are given in % by weight; q.s. = quantum satis (amount which is needed).

| Ingredient | Example | | |
|---|---|---|---|
| | 55 | 56 (comp.) | 57 (comp.) |
| Cetearyl alcohol | 4.0 | 4.0 | 4.0 |
| CTAC (cetrimonium chloride) | 0.2 | — | 2.0 |
| BTAC (behentrimonium chloride) | 0.8 | 2.0 | — |
| Example 1 | 1.0 | — | — |
| Preservative | q.s. | q.s. | q.s. |
| Water | Ad. 100 | Ad. 100 | Ad. 100 |

Use of the Rinse-Off Conditioning Composition

The same type of hair swatches as described for Example 7 and Example 8 are used. Swatches are pre-treated (base wash with a 14% by weight sodium lauryl ether sulfate (SLES) solution), and then treated with one of the conditioning compositions. The rinse-off hair conditioning compositions (Examples 14 to 55) are used according to the steps:
a) optionally applying a shampoo composition onto the hair;
b) optionally washing the hair with the shampoo composition;
c) optionally removing the shampoo composition from the hair;
d) applying the hair conditioning composition onto the hair;
e) removing (rinsing) said conditioning composition from the hair.

As a comparison, analogous conditioner compositions are used containing behentrimonium chloride (BTAC) according to the comparative Example 56, at the active level of 2.0% by weight (see composition in Table 5).

Wet and dry combing force are measured using the Diastron (UK) MTT175 (for dry combing—after at least 12 hours of drying time), swatches are pre-combed three times before the measurement. Table 6 presents the results of wet (average) combing force on virgin hair treated with conditioner compositions according to the invention of Examples 28, 30, 32, 48, 50, 52, and 55 (see compositions in Table 5). As comparison, an analogous conditioner composition is used containing behentrimmonium chloride according to Example 56 (BTAC) at 2% active by weight.

TABLE 6

Wet combing force (gmf) results of virgin hair treated with rinse-off conditioning compositions (Example 28, Example 31, Example 32, Example 48, Example 50, Example 52, and Example 55), compared to the comparative composition (2.0% BTAC).

| Composition | Wet combing force (average), gmf (virgin hair) |
|---|---|
| Example 56 (comp.) | 12.4 |
| Example 28 | 9.2 |
| Example 31 | 11.9 |
| Example 32 | 11.8 |
| Example 48 | 11.2 |
| Example 50 | 11.8 |
| Example 52 | 11.1 |
| Example 55 | 11.8 |

It is clearly seen that the wet combing force can be considerably improved compared to market standard BTAC containing compositions (comp.=comparative composition i.e. not pursuant to the present invention), by using compositions comprising estolide esters and reduced CTAC. Additionally, dry combing force of damaged (4 h bleached) hair is also lowered versus compositions comprising CTAC and no estolide esters, as shown in Table 7.

TABLE 7

Dry combing force (maximum, gmf) results of damaged hair treated with rinse-off conditioning compositions (Examples 28 and 31), compared to the comparative composition (2.0% CTAC, Example 57).

| Composition | Dry combing force (maximum), gmf (damaged hair) |
|---|---|
| Example 57 (comp.) | 4.8 |
| Example 28 | 4.5 |
| Example 31 | 4.7 |

Moreover, hair gloss is improved of both virgin and damaged hair after using estolide ester-containing hair conditioners, as illustrated in Table 8. The performance of new conditioners is compared to the CTAC-containing conditioner of Example 57.

TABLE 8

Hair shine measured by the Samba Hair System for virgin and damaged hair treated with hair conditioners containing estolide esters, as compared to hair treated with the comparative composition (2.0% CTAC, Example 57).

| Composition | Hair shine, virgin hair | Hair shine, damaged hair |
|---|---|---|
| Example 57 (comp.) | 18.7 | 8.3 |
| Example 28 | — | 9.4 |
| Example 30 | 19.4 | 10.9 |
| Example 31 | — | 9.6 |
| Example 32 | 18.9 | 9.4 |

EXAMPLE 58: STABILITY OF ESTOLIDE ESTERS IN COSMETIC PRODUCTS

Estolide esters could be expected to undergo hydrolysis in acidic environment. The shampoo and rinse-off hair conditioners of this invention are aqueous systems, the pH of which can be about pH 6 and pH 4, respectively. Due to hydrolysis, cosmetic but also household products formulated at acidic pH and containing ester compounds often show stability and/or performance decrease over time, due to chemical decomposition of the esters. However, the estolide molecules presented here in the compositions overcome this issue, and show excellent stability at low pH.

Exemplarily the solution of Example 1 in water with addition of SLES, showed 0.01% [mass/mass i.e. m/m] ricinoleic acid (as hydrolysis product) for the fresh sample, and no increase was noted after one week at 50° C. The value 0.01% [m/m] is the detection limit of the liquid chromatography method. Similarly, a finished hair conditioner product (Example 26) showed no increase in the ricinoleic acid content.

Therefore, the cosmetic compositions are found to be stable, showing no increase of ricinoleic acid as hydrolysis product.

Compounds of Formula (1) tend to undergo self-condensation, particularly when under acidic conditions, which may impact the storage stability of finished products at a pH<7. This can be avoided by using esterified estolides of Formula (3), such as Example 1 to Example 6b.

EXAMPLE 59: COMPARISON WITH HOSTAGLISS® L4

The structure of Hostagliss® L4 (of Clariant, Germany) is shown above in the reaction scheme for Example 1. It is a carboxylic acid. The wet and dry combing force required following treatment with a composition according to the present invention (59x) and two comparative compositions (59y and 59z) wherein 59y differs from 59x in that 59y contains the carboxylic acid Hostagliss® L4, whereas 59x is a non-negatively charged Component A according to the present invention.

TABLE 9

Wet and dry combing force (gmf) results of bleached hair treated with rinse-off conditioning compositions as explained below.

| | Example | | |
|---|---|---|---|
| | 59x | 59y (comp.) | 59z (comp.) |
| Cetearyl alcohol | 4.0 | 4.0 | 4.0 |
| CTAC (cetrimonium chloride) | 0.4 | — | 2.0 |
| Hostagliss ® L4 | — | 1.6 | — |
| Example 6b | 1.6 | — | — |
| Preservative | q.s. | q.s. | q.s. |
| Water | Ad. 100 | Ad. 100 | Ad. 100 |
| Wet combing force, gmf | 15.2 | 22.8 | 20.1 |
| Dry combing force, gmf | 16.7 | 42.4 | 33.1 |

It can thus be concluded that in view of the higher force required for combing using compositions 59y and 59z that the composition 59x, containing Component A of the present invention, has superior hair detangling and conditioning versus comparative compositions 59y and 59z. Furthermore, Hostagliss® L4 performed worse than a cationic surfactant as conditioning active indicating that the anionic charge of the carboxylic acid group repels hair and therefore cannot adhere to hair so well in order to carry out its conditioning function.

The invention claimed is:

1. A cosmetic composition comprising water,
   A) at least one estolide ester compound having the Formula (3) as component A:

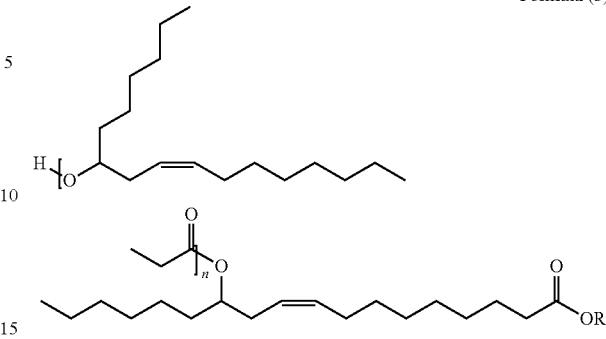

Formula (3)

wherein
   n is from 1 to 10, and
   R is selected from the group consisting of branched or linear $C_{3-20}$-alkyl,
   B) optionally at least one surfactant as component B,
   C) optionally at least one thickener as component C,
   D) optionally at least one hair conditioning as component D, and
   E) optionally at least one further component E, different to components A to D,
   with the proviso that the cosmetic composition contains at least one component B or at least one component D.

2. The cosmetic composition according to claim 1, wherein component A has a hydroxy value (OH value) from 1 to 60 mg KOH/g.

3. The cosmetic composition according to claim 1, wherein component A is used in an amount of from 0.1 to 10% by weight (based on the total weight of the composition) and wherein component A has a number average molecular weight (Mn) from 1100 to 3000 g/mol.

4. The cosmetic composition according to claim 1, wherein in Formula (3) n is from 2 to 8 and R is 2-ethylhexyl or decanyl.

5. The cosmetic composition according to claim 1, comprising from 5 to 20% by weight (based on the total weight of the composition) of at least one component B and from 0.01 to 5% by weight (based on the total weight of the composition) of at least one component C for the use as a hair shampoo composition.

6. The cosmetic composition according to claim 1, comprising from 0.1 to 10% by weight (based on the total weight of the composition) of at least one component D but not comprising a component C, for the use as a hair conditioning composition.

7. The cosmetic composition according to claim 1, comprising at least one component B and at least one component D for the use as a combination product as hair shampoo/conditioning composition.

8. The cosmetic composition according to claim 1, comprising at least one component B and/or at least one component D for the use as a leave-on conditioning composition.

9. A process for preparing a cosmetic composition, in particular a hair shampoo and/or conditioning composition, comprising the step of mixing at least one compound of Formula (3)

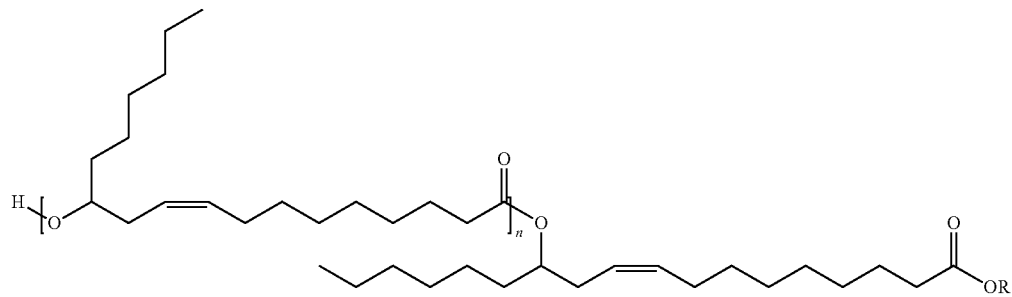

Formula (3)

wherein
n is from 1 to 10, and
R is selected from the group consisting of branched or linear $C_{3-20}$-alkyl, and water and at least one further surfactant component B or a hair conditioning component D, and optionally further components, a thickener component C and/or optionally a further component E, different to components A to D.

10. A method of treating the hair, comprising the steps of applying a hair shampoo and/or conditioning composition onto wet hair, lathering and removing said shampoo and/or conditioning composition from the hair, wherein the hair shampoo and/or conditioning composition comprises at least one estolide compound of Formula (3)

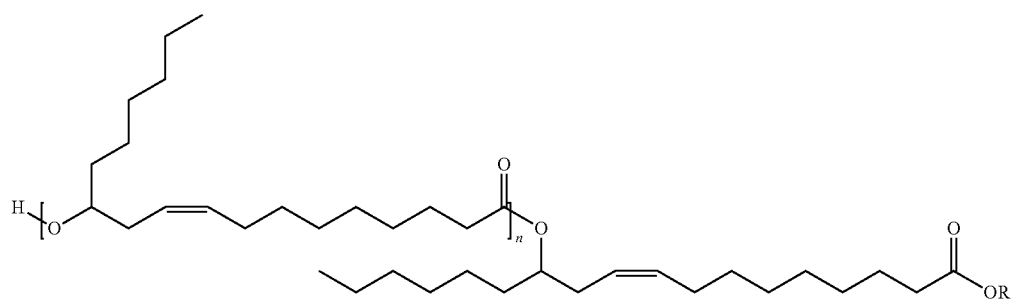

Formula (3)

wherein
n is from 1 to 10, and
R is selected from the group consisting of branched or linear $C_{3-20}$-alkyl, optionally a surfactant component B, optionally a thickener component C, optionally a hair conditioning component D, and optionally a further component E, different to components A to D, with the proviso that the shampoo and/or conditioning composition contains at least one component B or at least one component D.

11. The method of treating the hair according to claim 10, comprising the following steps:
a) applying a hair shampoo composition onto the hair;
b) washing the hair with the hair shampoo composition;
c) removing the hair shampoo composition from the hair;
d) applying a conditioning composition onto wet hair;
e) rinsing said conditioning composition from the hair, wherein the shampoo and/or conditioning composition comprises at least one compound of Formula (3).

12. The method according to claim 10, wherein the shampoo and/or conditioning composition comprises at least one surfactant component B, which is selected from the group consisting of anionic surfactants, non-polymeric, and cationic quaternary ammonium compounds.

13. The method according to claim 10, wherein the shampoo and/or conditioning composition comprises at least one component D.

14. The method according to claim 10, wherein the shampoo and/or conditioning composition is applied to the hair on a weekly to bi-weekly basis, following initial treatment of the hair with a shampoo composition.

15. The method according to claim 11, wherein the shampoo and/or conditioning composition comprises at least one surfactant component B, which is selected from the group consisting of anionic surfactants, non-polymeric, and cationic quaternary ammonium compounds.

16. The method according to claim 10, wherein the shampoo and/or conditioning composition comprises at least one component D selected from the group consisting of CTAC (cetrimonium chloride) and BTAC (behentrimonium chloride).

17. The method according to claim 11, wherein the shampoo and/or conditioning composition comprises at least one component D.

18. The method according to claim 11, wherein the shampoo and/or conditioning composition comprises at least one component D selected from the group consisting of CTAC (cetrimonium chloride) and BTAC (behentrimonium chloride).

19. The method according to claim 11, wherein the shampoo and/or conditioning composition is applied to the hair on a weekly to bi-weekly basis, following initial treatment of the hair with a shampoo composition.

20. A method of treating the hair, comprising the steps of applying a leave-on conditioning composition onto dry or wet hair, wherein the leave-on conditioning composition comprises at least one estolide ester compound of Formula (3)

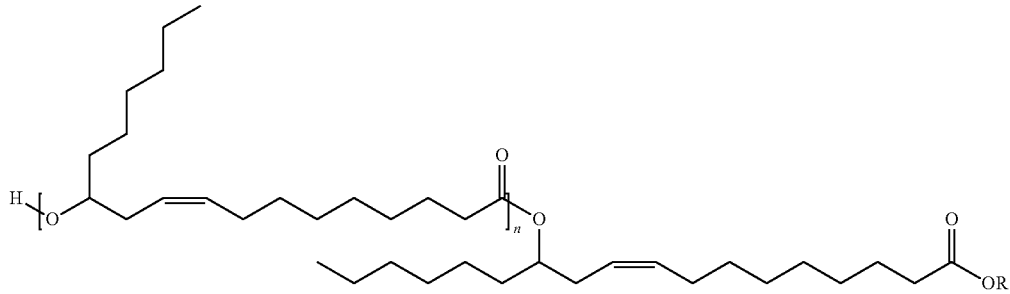

Formula (3)

wherein n is from 1 to 10, and

R is selected from the group consisting of branched or linear $C_{3-20}$-alkyl, optionally a surfactant component B, optionally a thickener component C, at least one hair conditioning component D, and optionally a further component E, different to components A to D, and b) if necessary drying the hair, wherein said a leave-on conditioning composition is applied to the hair on a daily to weekly basis.

* * * * *